United States Patent
Ribble et al.

(10) Patent No.: US 9,456,780 B2
(45) Date of Patent: Oct. 4, 2016

(54) DYNAMIC THERAPY DELIVERY SYSTEM

(71) Applicant: Hill-Rom Services, Inc., Batesville, IN (US)

(72) Inventors: David L. Ribble, Indianapolis, IN (US); Laetitia Gazagnes, Montpellier (FR); Charles A. Lachenbruch, Lakeway, TX (US)

(73) Assignee: Hill-Rom Services, Inc., Batesville, IN (US)

( * ) Notice: Subject to any disclaimer, the term of this patent is extended or adjusted under 35 U.S.C. 154(b) by 181 days.

(21) Appl. No.: 14/171,800

(22) Filed: Feb. 4, 2014

(65) Prior Publication Data

US 2014/0221962 A1    Aug. 7, 2014

Related U.S. Application Data

(60) Provisional application No. 61/762,022, filed on Feb. 7, 2013.

(51) Int. Cl.
*A61G 7/00* (2006.01)
*A61B 5/00* (2006.01)
*A61M 5/172* (2006.01)
(Continued)

(52) U.S. Cl.
CPC .......... *A61B 5/4839* (2013.01); *A47C 27/081* (2013.01); *A61B 5/6892* (2013.01); *A61G 7/047* (2013.01); *A61M 5/1723* (2013.01); *A61M 2205/3303* (2013.01); *A61M 2205/3317* (2013.01)

(58) Field of Classification Search
CPC .......... A61B 5/6892; A61B 10/0064; A61B 2562/247; A61B 5/1115; A61B 5/1477; A61B 5/4266; A61B 5/4272; A61B 5/4806; A61B 5/4809; A61B 5/4812; A61B 5/4839; A61M 2205/3303; A47C 21/044; A47C 21/04; A47C 27/006; A47C 27/007
See application file for complete search history.

(56) References Cited

U.S. PATENT DOCUMENTS 4,786,295 A  * 11/1988 Newman ............ B01D 46/0023
                                                340/607
5,140,985 A     8/1992 Schroeder et al.
(Continued)

FOREIGN PATENT DOCUMENTS

IT   WO 2005042038 A1 *  5/2005  ............... A61L 9/14
WO      WO 03/075761 A2    9/2003
(Continued)

OTHER PUBLICATIONS

EP Search Report for Application 13167537.3: mailed Aug. 2, 2013. Place of Search—The Hague: Date of Completion of the Search—Jul. 24, 2013.
(Continued)

*Primary Examiner* — Kevin C Sirmons
*Assistant Examiner* — William Carpenter
(74) *Attorney, Agent, or Firm* — Barnes & Thornburg LLP

(57) ABSTRACT

Systems for delivery of therapeutic agents and related methods are disclosed. A sensing system is configured to detect a chemical in the vicinity of a patient and transmit a signal to a controller upon detection. A controller is configured to release a therapeutic agent which is transported to the site of interest. The controller communicates with an electronic medical records database, an alarm and a nurse call system.

16 Claims, 12 Drawing Sheets

(51) Int. Cl.
*A47C 27/08* (2006.01)
*A61G 7/047* (2006.01)

(56) References Cited

U.S. PATENT DOCUMENTS

| | | | | |
|---|---|---|---|---|
| 5,144,284 A | * | 9/1992 | Hammett | A61B 5/1115 128/886 |
| 5,355,540 A | * | 10/1994 | Allen | A61G 7/0005 4/547 |
| 6,309,351 B1 | | 10/2001 | Kurnik et al. | |
| 7,076,371 B2 | * | 7/2006 | Fu | A61B 5/082 702/19 |
| 8,181,290 B2 | * | 5/2012 | Brykalski | A47C 21/044 5/421 |
| 8,672,842 B2 | * | 3/2014 | Kenalty | A61B 5/0015 324/691 |
| 2003/0116020 A1 | * | 6/2003 | Hedstrom | B01D 46/002 95/286 |
| 2004/0255937 A1 | | 12/2004 | Sun | |
| 2005/0082175 A1 | | 4/2005 | Saini et al. | |
| 2005/0096559 A1 | * | 5/2005 | Yanai | A61B 5/113 600/534 |
| 2005/0190068 A1 | * | 9/2005 | Gentry | A61B 5/11 340/665 |
| 2005/0274170 A1 | | 12/2005 | Shekarriz et al. | |
| 2006/0025663 A1 | * | 2/2006 | Talbot | A61B 5/0002 600/365 |
| 2006/0068490 A1 | | 3/2006 | Tang et al. | |
| 2006/0205061 A1 | | 9/2006 | Roukes | |
| 2006/0216209 A1 | | 9/2006 | Braig et al. | |
| 2007/0056101 A1 | * | 3/2007 | Mahajan | A61G 7/057 5/600 |
| 2007/0088334 A1 | * | 4/2007 | Hillis | A61B 5/0002 604/891.1 |
| 2007/0213657 A1 | * | 9/2007 | Jennewine | A61B 5/0031 604/66 |
| 2007/0261548 A1 | | 11/2007 | Vrzalik et al. | |
| 2010/0248268 A1 | | 9/2010 | Woods et al. | |
| 2011/0054273 A1 | | 3/2011 | Omoda | |
| 2012/0036636 A1 | * | 2/2012 | Stryker | A61G 7/001 5/600 |
| 2012/0053424 A1 | * | 3/2012 | Kenalty | A61B 5/0015 600/300 |
| 2012/0108924 A1 | | 5/2012 | Baker, Jr. et al. | |
| 2012/0183949 A1 | * | 7/2012 | Hyde | A61B 5/082 435/5 |
| 2012/0279090 A1 | * | 11/2012 | Zecca | A43B 1/00 36/3 B |
| 2013/0091757 A1 | * | 4/2013 | Victorio da Costa | A01M 13/00 43/125 |
| 2013/0227783 A1 | | 9/2013 | Brykalski et al. | |
| 2013/0309713 A1 | * | 11/2013 | Ribble | A61B 5/6892 435/34 |
| 2013/0317399 A1 | * | 11/2013 | Ribble | G06F 19/3431 601/84 |

FOREIGN PATENT DOCUMENTS

WO  WO 2005/025413 A2  3/2005
WO  WO 2012/122267 A1  9/2012

OTHER PUBLICATIONS

Early Warning Inc.—Technologies: Early Warning Pathogen Sensor: Literature from Internet.

* cited by examiner

DYNAMIC THERAPY DELIVERY SYSTEM

CROSS REFERENCE TO RELATED APPLICATIONS

The present application claims the benefit, under 35 U.S.C. §119(e), of U.S. Provisional Application No. 61/762,022, which was filed Feb. 7, 2013, and which is hereby incorporated by reference herein in its entirety.

BACKGROUND

Delivery of therapeutic agents upon detection of chemicals and odors in the vicinity of a patient supported by a person support apparatus is a continuing challenge. Chemicals and/or biomarkers of a patient may be indicative of presence of conditions, the rate of change in development of certain conditions and/or onset of other conditions. While several systems exist to deliver therapeutic agents, a need exists to continue development in this area.

BRIEF SUMMARY

The present disclosure includes one or more of the features recited in the appended claims and/or the following features which, alone or in any combination, may comprise patentable subject matter.

One embodiment of a system may comprise a sensor configured to generate a signal in response to a chemical. A control system may be configured to receive the signal from the sensor and control flow of a therapeutic agent from a therapeutic agent repository to a site.

Another embodiment of a system may comprise a person support apparatus. A sensor may be configured to generate a signal in response to at least one chemical in secretion from a person supported by the person support apparatus. A control system may be configured to receive the signal and control flow of a therapeutic agent from a therapeutic agent reservoir to site of the secretion.

One method may comprise sensing a chemical in a secretion, determining whether a concentration of the chemical is greater than a predetermined threshold and releasing a therapeutic agent to a site of the secretion if the concentration of the chemical is greater than the predetermined threshold.

One embodiment of a therapeutic device may comprise means for generating a signal in response to a chemical in a secretion and means for controlling flow of a therapeutic agent to site of said secretion based on said signal.

One embodiment of a system may comprise a sensor configured to generate a signal in response to a chemical in a secretion. A control system may be configured to receive the signal from the sensor and control flow of a therapeutic agent from a therapeutic agent repository to a site of the secretion.

Additional features, which alone or in combination with any other feature(s), such as those listed above and those listed in the claims, may comprise patentable subject matter and will become apparent to those skilled in the art upon consideration of the following detailed description of various embodiments exemplifying the best mode of carrying out the embodiments as presently perceived.

BRIEF DESCRIPTION OF DRAWINGS

The accompanying drawings incorporated in and forming a part of the specification illustrate several aspects of the claimed subject matter and, together with the description, serve to explain the principles of the claimed subject matter. In the drawings:

DETAILED DESCRIPTION OF ILLUSTRATIVE EMBODIMENTS

Figure 1:
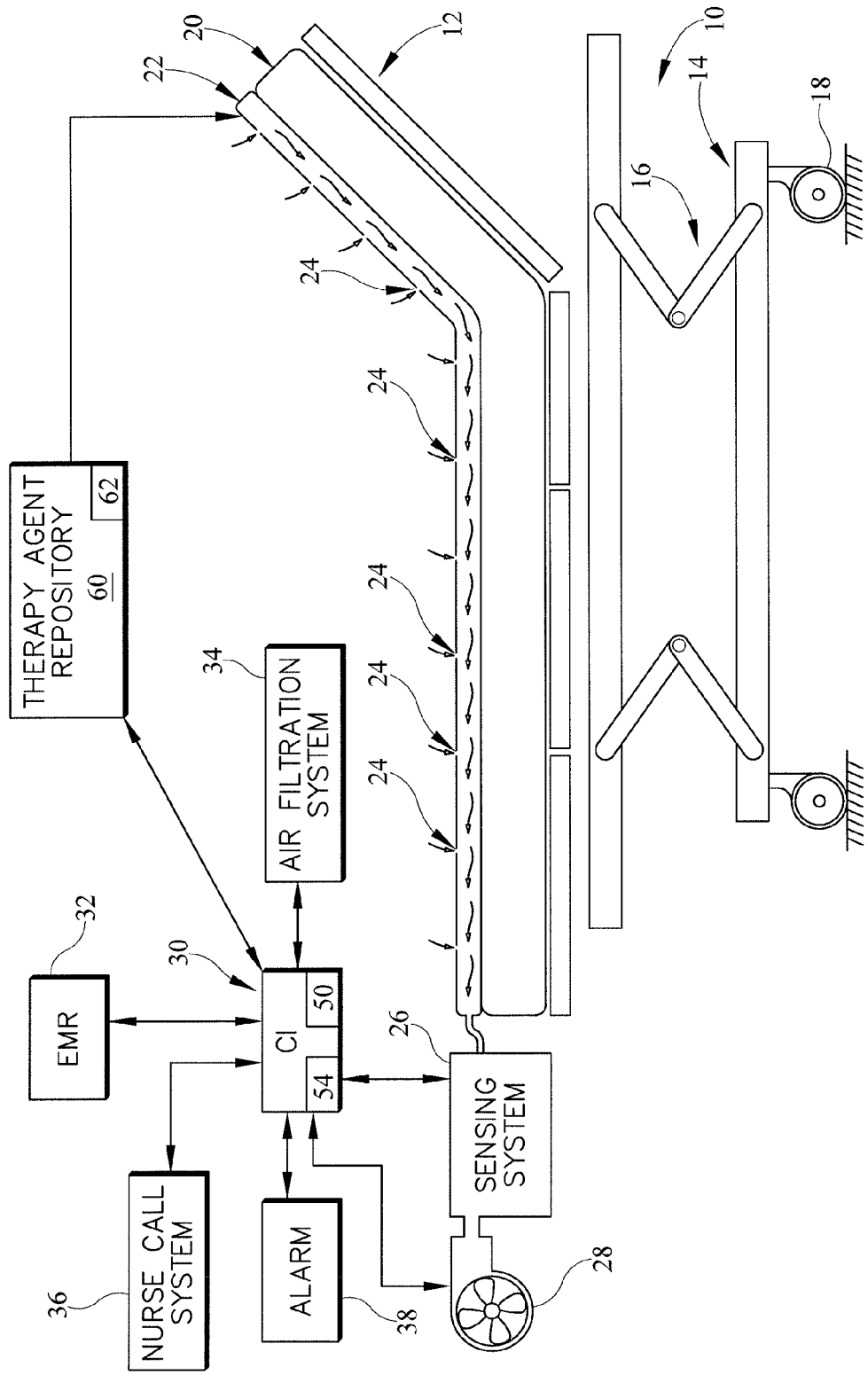
FIG. 1 is a block diagram of a system for delivery of therapeutic agents wherein a portion of the fluid transport system comprises a mattress topper, constructed according to one or more of the principles disclosed herein.

The embodiments of the claimed subject matter and the various features and advantageous details thereof are explained more fully with reference to the non-limiting embodiments and examples that are described and/or illustrated in the accompanying drawings and detailed in the following description. It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be briefly mentioned or omitted so as to not unnecessarily obscure the embodiments of the claimed subject matter described. The examples used herein are intended merely to facilitate an understanding of ways in which the claimed subject matter may be practiced and to further enable those of skill in the art to practice the embodiments of the claimed subject matter described herein. Accordingly, the examples and embodiments herein are merely illustrative and should not be construed as limiting the scope of the claimed subject matter, which is defined solely by the appended claims and applicable law. Moreover, it is noted that like reference numerals represent similar parts throughout the several views of the drawings.

It is understood that the subject matter claimed is not limited to the particular methodology, protocols, devices, apparatus, materials, applications, etc., described herein, as these may vary. It is also to be understood that the terminology used herein is used for the purpose of describing particular embodiments only, and is not intended to limit the scope of the claimed subject matter.

Unless defined otherwise, all technical and scientific terms used herein have the same meanings as commonly understood by one of ordinary skill in the art.

One embodiment of a system to detect a chemical in the vicinity of a person support apparatus 10 is shown in FIG. 1. In this embodiment, the person support apparatus 10 is a bed, however, in other embodiments the person support apparatus 10 may be a wheelchair, stretcher or any other apparatus configured to support a person thereon. The person support apparatus 10 in this embodiment comprises an upper frame 12 which is supported over a lower frame 14 by supports 16. The upper frame 12 comprises one of more sections and the supports 16 are configured to variably elevate at least one section of the upper frame 12 with respect to the lower frame 14. The lower frame 14 rests on at least one caster wheel 18 in this embodiment, allowing the person supported apparatus 10 to be transported. A person support surface 20 rests on the person support apparatus 10. In this embodiment the person support surface 20 is a mattress and comprises fluid filled bladders, in other embodiments the person support surface may be made of any combination of bladders, foam and other polymeric materials. A mattress topper 22 is configured to be positioned on top of the person support surface 20 such that a person can be supported on top of the mattress topper 22. The mattress topper 22 comprises fluid permeable pores 24 on its surface which is configured to support a person. Fluid permeable pores 24 are configured to allow air, water and microbial particles to pass through them. A pump 28 is configured to suck fluid in through the fluid permeable pores 24 and into a sensing system 26 through a fluidic connection as shown in FIG. 1. The pump 28 is configured to perform one or more functions of the person support surface 20 including but not limited to inflation of bladders. In another embodiment the pump 28 is dedicated for use by the system to detect chemicals. In this embodiment the sensing system 26 comprises electrodes whose surfaces are polymerized. The constitution of the surroundings effect the electrical resistance measured between the electrodes and this change in resistance is used to identify the constitution of the surroundings by comparison with known resistance and/or change in resistance values.

In other embodiments, any other type of sensors may be used including but not limited to metal oxide type semiconductor (MOS) sensors, capacitive sensors, and inductive sensors and surface acoustic wave devices. In another embodiment, protein based biosensors such as odarant binding proteins (OBPs), sensory appendage proteins (SAPs), odorant or gustatory receptors, serpentine receptors and/or odarant degrading enzymes (ODEs) may be used along with electrochemical transducers to generate an electrical signal in response to detection of a chemical.

The pump 28 and the sensing system 26 are configured to communicate with a control interface (CI) 30. In this embodiment, the control interface (CI) 30 comprises a memory 50 to store information supplied by the sensing system 26 for a predetermined time, a processor 54 to process information and a display (not shown). Memory 50 may be of any type including volatile and non-volatile. In this embodiment the CI 30 is mounted on the person support apparatus 10 and controls the function of one or more features of the person support apparatus 10. In another embodiment, the system comprises a dedicated CI 30. The CI 30 is configured to communicate with a nurse call system 36 configured to alert a caregiver. The CI 30 in this embodiment is also configured to activate an alarm 30. Alarm 30 is an audio alert in this embodiment. In other embodiments, alarm 30 may be any combination of audio, visual and/or tactile alerting systems. The CI 50 is also configured to communicate with an electronic medical records (EMR) database 32 in this embodiment. In this embodiment, the CI 30 is configured to communicate with an air filtration system 34. The CI 30 is configured to control the air filtration system 34 based on the results provided by the sensing system 26. In one prophetic example, if a high concentration of sweat is detected in the data transmitted by the sensing system 26 to the CI 30, the partial pressure of water vapor and/or temperature and/or volume of air being supplied to the room housing are modified to induce an environment to optimize sweat production. In another prophetic example, the air filtration system 34 comprises a controllable valve so as to prevent any air from leaking out of the room containing a patient without first cleansing the air if a determination is made that the data from the sensing system 26 indicates presence of a certain chemical above a predetermined threshold. The air filtration system 34 may rely on any combination of ionization, electrostatic and mechanical filtration technologies. In the embodiment shown in FIG. 1, the CI 30 is configured to communicate with a therapy agent repository 60 and a therapy agent repository pump 62. In this embodiment, the CI 30 is configured to control the therapy agent repository pump 62 to supply a therapeutic agent from the therapeutic agent repository 60 to a site such that the therapeutic agent can act on a person. In one prophetic example, in the embodiment shown in FIG. 1, if the sensing system 26 detects an indication of Ischemia (based on any indication including but not limited to $CO_2$, Urea, Urate, Chloride, Lactic Acid, $CO_2/O_2$ and O2) a vasodilator (including but not limited to histamines, niacin, potassium and compounds and nitric acid) is supplied in response. Any other therapeutic agent may be delivered in other embodiments including but not limited to an analgesic in response to recognition of an indicator of pain.

During operation of the system shown in FIG. 1, the CI 30 is configured to control the operation of the pump 28 to create a suction pressure allowing suction of fluids through the fluid permeable pores 24 and into the sensing system 26. In this embodiment, the sensing system 26 communicates with the CI 30 and supplies to the CI 30 results of the testing on the fluid flowing into the sensing system 26. The CI 30 in this embodiment allows a caregiver to set thresholds for presence of one or more chemicals. The thresholds may be set in the form of limits or a rate of change. In another embodiment, the caregiver may program detection of specific combinations of chemicals as a threshold. These thresholds are stored in the memory 50 in this embodiment. When results obtained from the sensing system 26 indicate that a predetermined threshold has been exceeded, the CI 30 activates alarm 38 in this embodiment. Once the CI 30 detects that the predetermined threshold has been exceeded, it commands to the therapy agent repository pump 62 to supply a therapeutic agent. In this embodiment, the therapeutic agent repository pump 62 supplies a therapeutic agent to the mattress topper 22. In this embodiment, when the therapeutic agent repository pump 62 functions, the pump 28 is configured to stop functioning thereby allowing the therapeutic agent to flow out of the fluid permeable pores 24. In another embodiment, the therapeutic agent repository pump 62 is configured to deliver the therapeutic agent to the surface of the mattress topper 22 thereby wetting it by capillary action.

The CI 30 also communicates with a nurse call system 36 when the predetermined threshold has been exceeded. In this embodiment the CI 30 logs the results of testing provided by the sensing system 26 and/or time and dosage of therapeutic agent supplied in an EMR 32 database, while in another embodiment, the CI 30 obtains information from the EMR 32 which is used to determine the thresholds. The thresholds may be so selected that presence of any chemical or combinations of chemicals may be sought for detection. In this embodiment, chemical signatures indicative of disease causing micro-organisms and/or vectors are sensed by the sensing system 26. In another embodiment, results supplied by the sensing system 26 are evaluated by the control interface 30 to seek chemical signatures indicative of biochemical markers of wound development such as IL-1α and Creatine Phosphokinase (CPK).

The sensing system 26 is contemplated to use other technologies in other embodiments, including but not limited to optical sensing, pulse oximetry and ultrasound.

Figure 2:
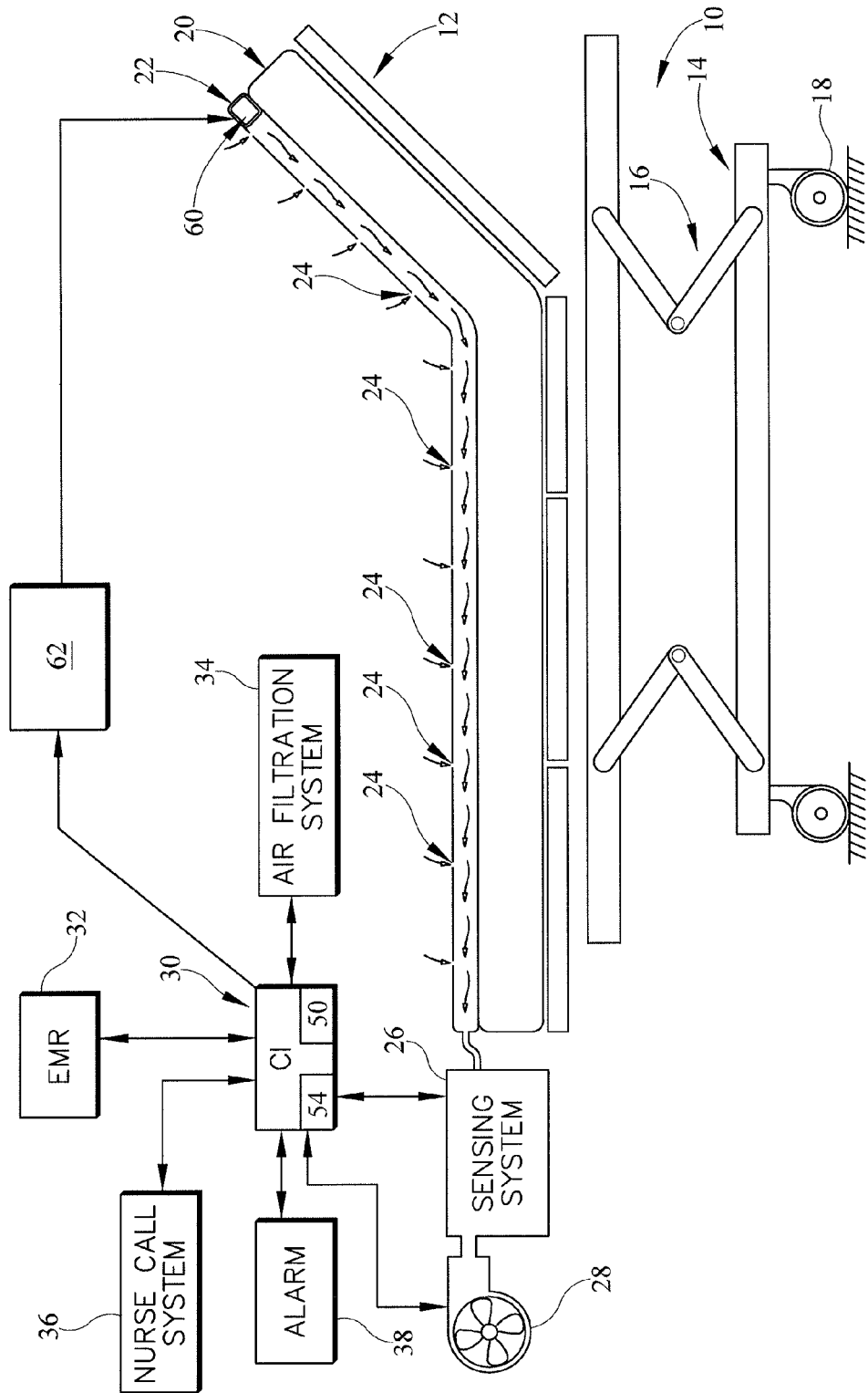
FIG. 2 is a block diagram of another system for delivery of therapeutic agents wherein at least a portion of the chemical sensor is housed within a mattress topper, constructed according to one or more of the principles disclosed herein.

In the embodiment of a system to detect a chemical in the vicinity of a person support apparatus 10 shown in FIG. 2, the sensing system 26 is housed within the mattress topper 22. In another embodiment the pump 22 is also housed within the mattress topper 22. The person support surface 20 in another embodiment comprises fluid permeable pores 24 and provides the fluidic path between the fluid permeable pores 24 and the sensing system 26.

Figure 3:
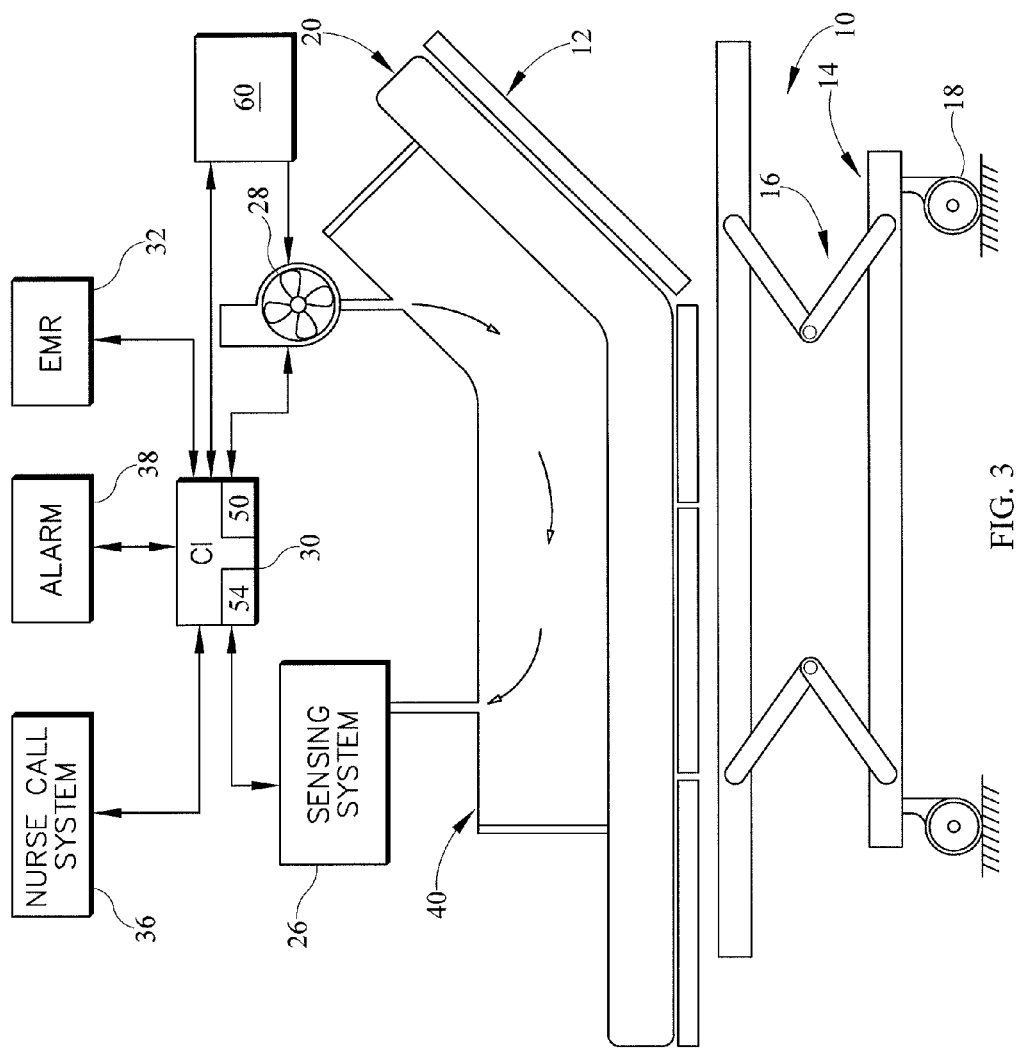
FIG. 3 is a block diagram of another system for delivery of therapeutic agents wherein a chemical containment screen is configured to envelope at least a portion of a patient supported by a person support apparatus, constructed according to one or more of the principles disclosed herein.

In FIG. 3, another embodiment of a system to detect a chemical in the vicinity of a person is depicted. In the system shown in FIG. 3, a chemical containment screen 40 is placed over the person support surface 20. The chemical containment screen is made of a substantially fluid impermeable material and is configured to fit over at least a portion of a person supported by the person support apparatus 20. The pump 28 is controlled by CI 30 and supplies air with a positive pressure within the volume of air contained by the chemical containment screen 40. The sensing system 26 is in fluidic communication with the volume of air contained by the chemical containment screen 40. The sensing system 26 is configured to communicate with a CI 30 which comprises a memory 50. The CI 30 is also configured to communicate with a nurse call system 36, an alarm 38 and an EMR 32 in this embodiment. In the embodiment shown in FIG. 3, the pump 28 is configured to supply a therapeutic agent from the therapeutic agent repository 60 into the volume of air inside the chemical containment screen 40 along with air.

Figure 4:
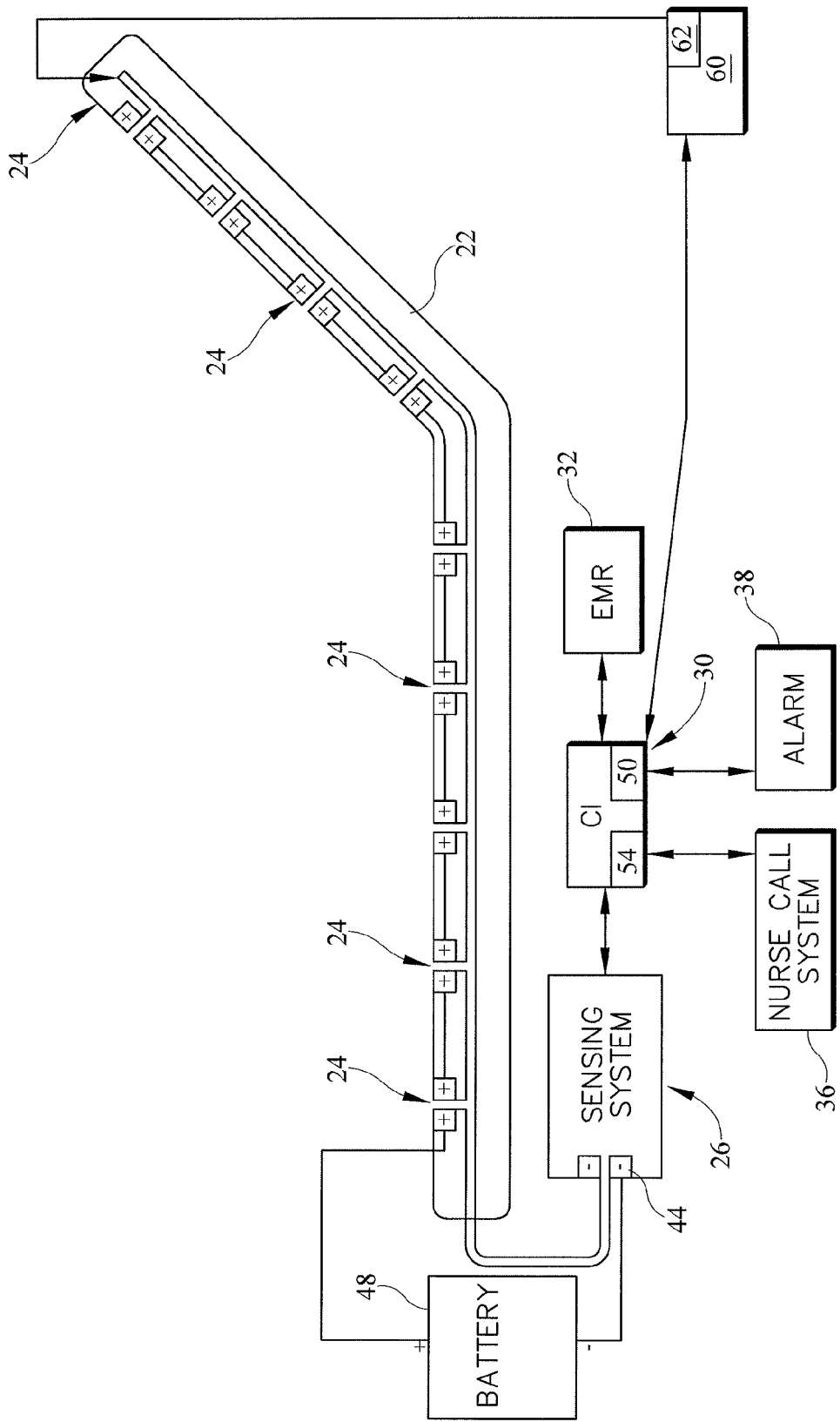
FIG. 4 is a block diagram of another system for delivery of therapeutic agents wherein at electric potential is used to generate fluid flow in a fluid transport system, constructed according to one or more of the principles disclosed herein.

In the embodiment of a system to detect a chemical in the vicinity of a person support apparatus 10 shown in FIG. 4, an electrical potential is used to induce flow of fluid between fluid permeable pores 24 and the sensing system 26. FIG. 4 shows a mattress topper 22 which comprises positively charged electrical leads 42 attached substantially close to the inlet of the fluid permeable pores 24 in this embodiment. Negatively charged electrical leads 44 are attached to the sensing system 26. The positively charged electrical leads 42 and negatively charged electrical leads 44 are attached to the positive and negative terminals of a battery 48, respectively. The battery 48 and electrical leads form a differential in electrical potential between the fluid permeable pores 24 and the sensing system 26. Particulate, volatile and liquid matters are drawn through the fluidic connection between the fluid permeable pores 24 and the sensing system 26 based on their electrophoretic mobility. In one embodiment, the CI 30 provides electrical potential between the positively charged electrical leads 42 and the negatively charged electrical leads 44 instead of utilization of a battery 48. The sensing system 26 is in communication with a CI 30 comprising a memory 50. The CI 30 is configured to communicate with an EMR 32, nurse call system 36 and an alarm 38 in this embodiment. In another embodiment the fluid permeable pores 24, positively charged electrical leads 42 and the fluidic path to the sensing system 26 are incorporated in a person support surface 20. The therapeutic agent is supplied by the therapeutic agent pump 62 from the therapeutic agent repository 60 to the mattress topper 22.

Figure 5:
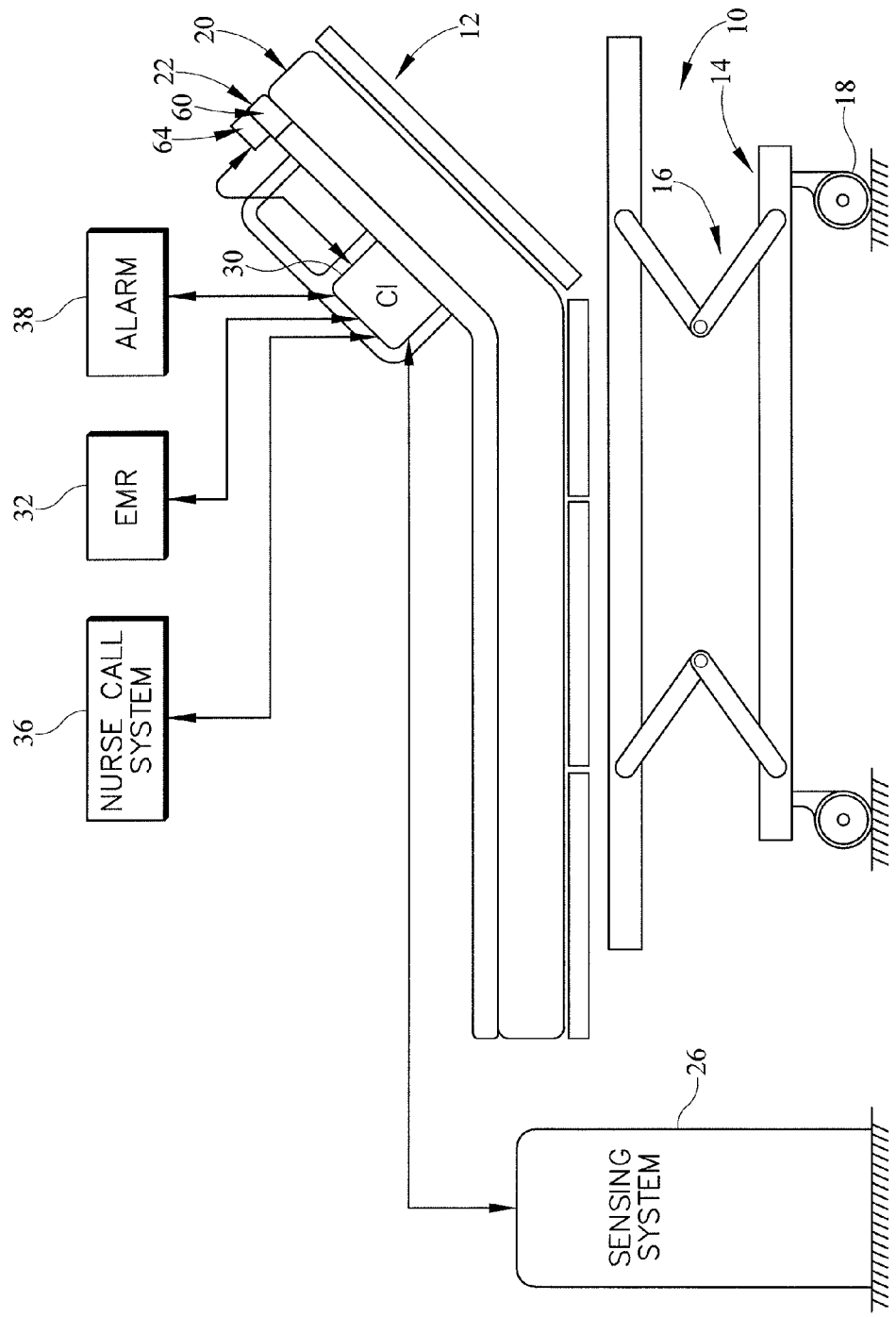
FIG. 5 is a block diagram of a system for delivery of therapeutic agents wherein the sensing system is a free standing device, constructed according to one or more of the principles disclosed herein.

In the embodiment shown in FIG. 5, a standalone sensing system 26 samples air circulating around a person support apparatus and is configured to communicate the sensed data to a CI 30 of a person support apparatus 10. The standalone sensing system 26 may be a free standing structure resting on the floor, be mounted on the person support apparatus 10 or be supported by any other structure in the vicinity of the person support apparatus 10. CI 30 is configured to communicate with a nurse call system 36, EMR 32 and an alarm 38. The therapeutic agent repository valve 64 is configured to be controlled by the CI 30 and release therapeutic agent from the therapeutic agent repository 60.

Figure 6:
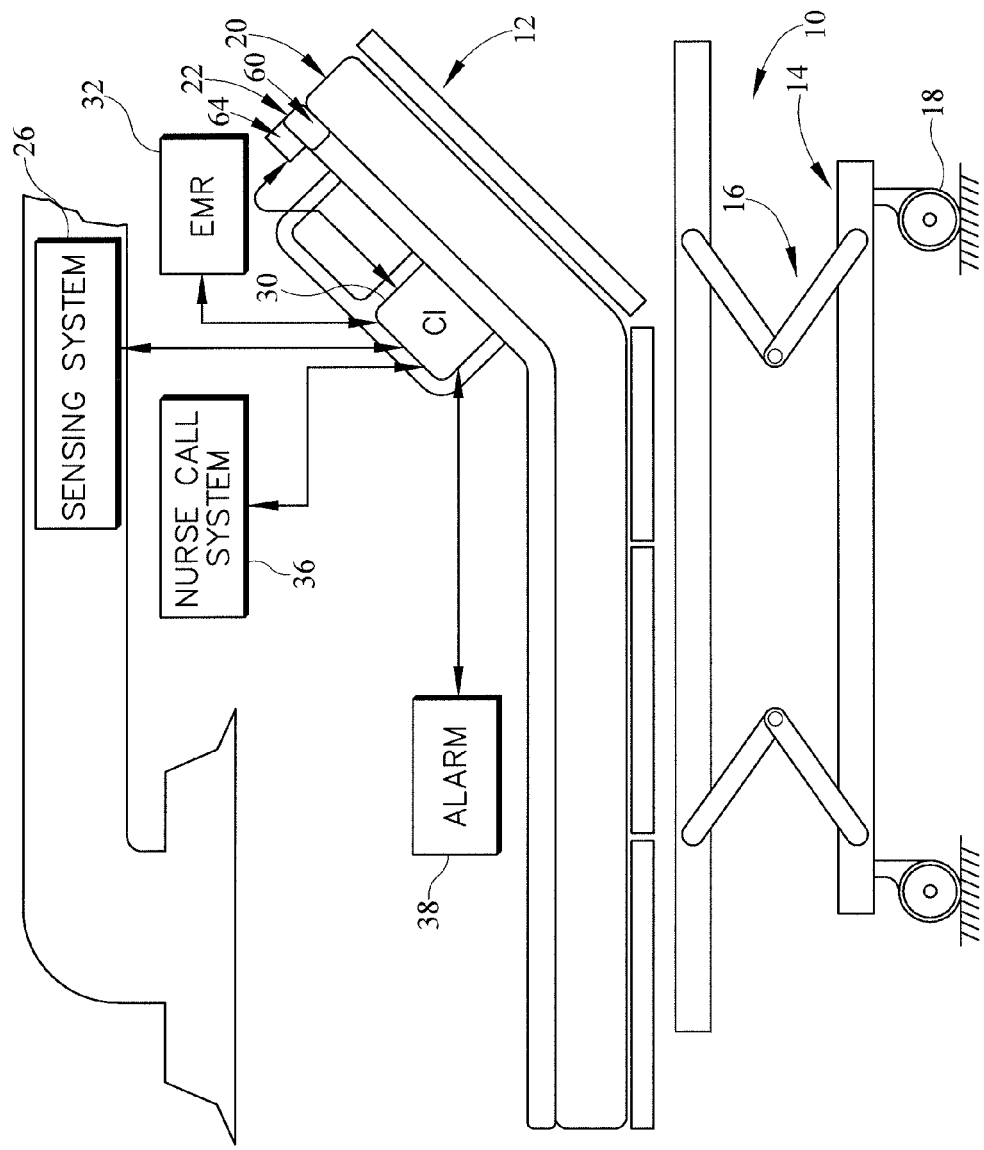
FIG. 6 is a block diagram of another system for delivery of therapeutic agents wherein the sensing system is housed within the air filtration system, constructed according to one or more of the principles disclosed herein.

In another embodiment shown in FIG. 6, the sensing system 26 is housed within the air filtration system 34. Air filtration system 34 is the heating, ventilation and air conditioning (HVAC) system of the room which houses the person support apparatus 10. The sensing system 26 samples air flowing through the air filtration system 34 and is configured to communicate the sensed data to a CI 30 of a person support apparatus 10. The CI 30 is configured to control the air filtration system 34 based on the results provided by the sensing system 26. In one prophetic example, if a high concentration of sweat is detected in the data transmitted by the sensing system 26 to the CI 30, the partial pressure of water vapor and/or temperature and/or volume of air being supplied to the room housing are modified to induce an environment to optimize sweat production. In another prophetic example, the air filtration system 34 comprises a controllable valve so as to prevent any air from leaking out of the room containing a patient without first cleansing the air if a determination is made that the data from the sensing system 26 indicates presence of a certain chemical above a predetermined threshold. CI 30 is configured to communicate with a nurse call system 36, EMR 32, therapeutic agent repository valve 64 and an alarm 38.

Figure 7:
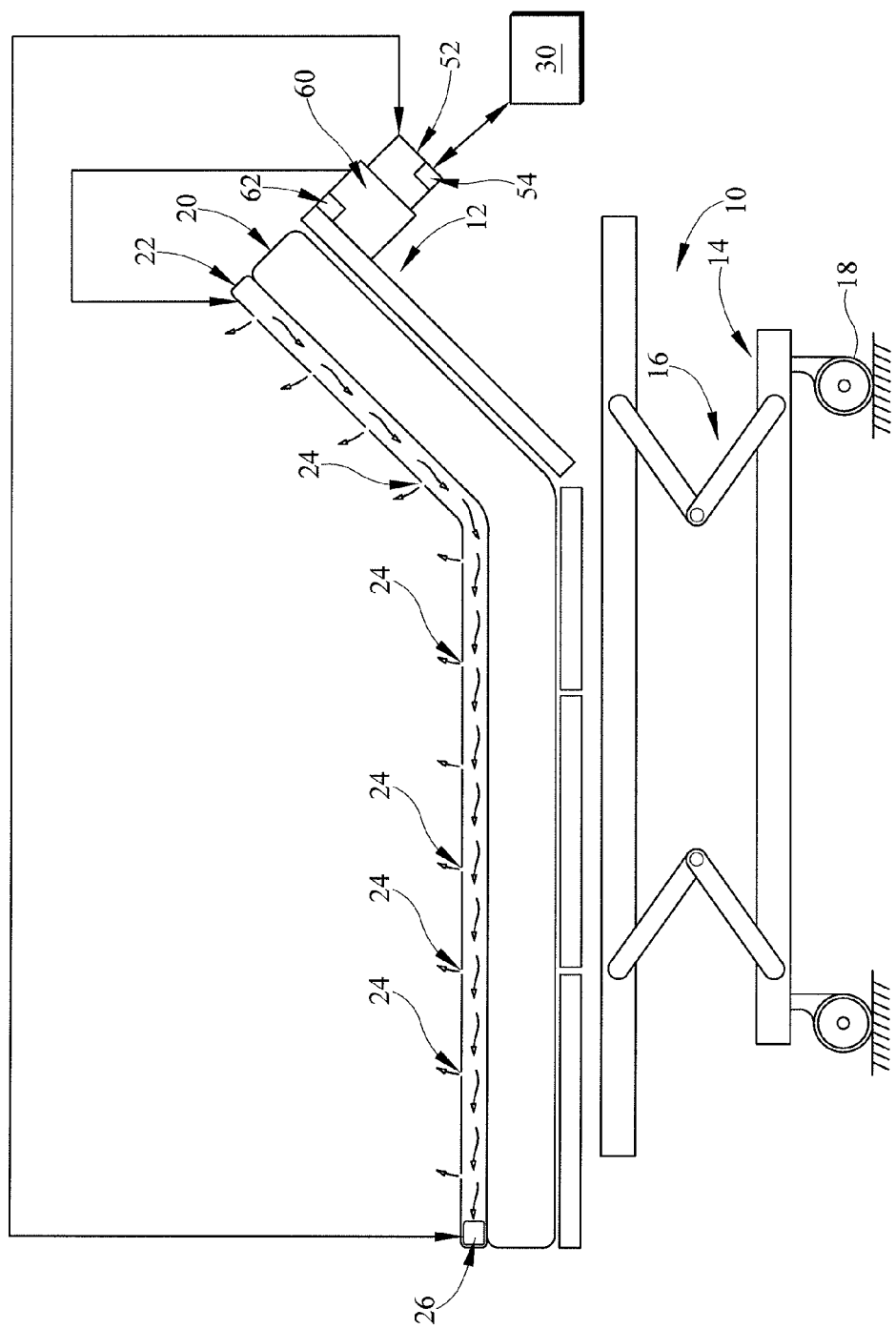
FIG. 7 is a block diagram of another system for delivery of therapeutic agents wherein the therapy agent repository is mounted on the person support apparatus, constructed according to one or more of the principles disclosed herein.

FIG. 7 shows controller 52 in communication with a control interface 30, sensing system 26 and a therapy agent repository pump 62. In the embodiment shown in FIG. 7, the controller 52 comprises processor 54 which is configured to control the operation of the therapy agent repository pump 62 while the control interface 30 allows a user to vary parameters, including but not limited to the threshold of chemical in response to which the therapeutic agent is released. In the embodiment shown in FIG. 7, the sensing system 26 is integrated into the mattress topper 22 while the therapy agent repository 60 and the controller 52 are mounted on the person support apparatus 10.

Figure 8:
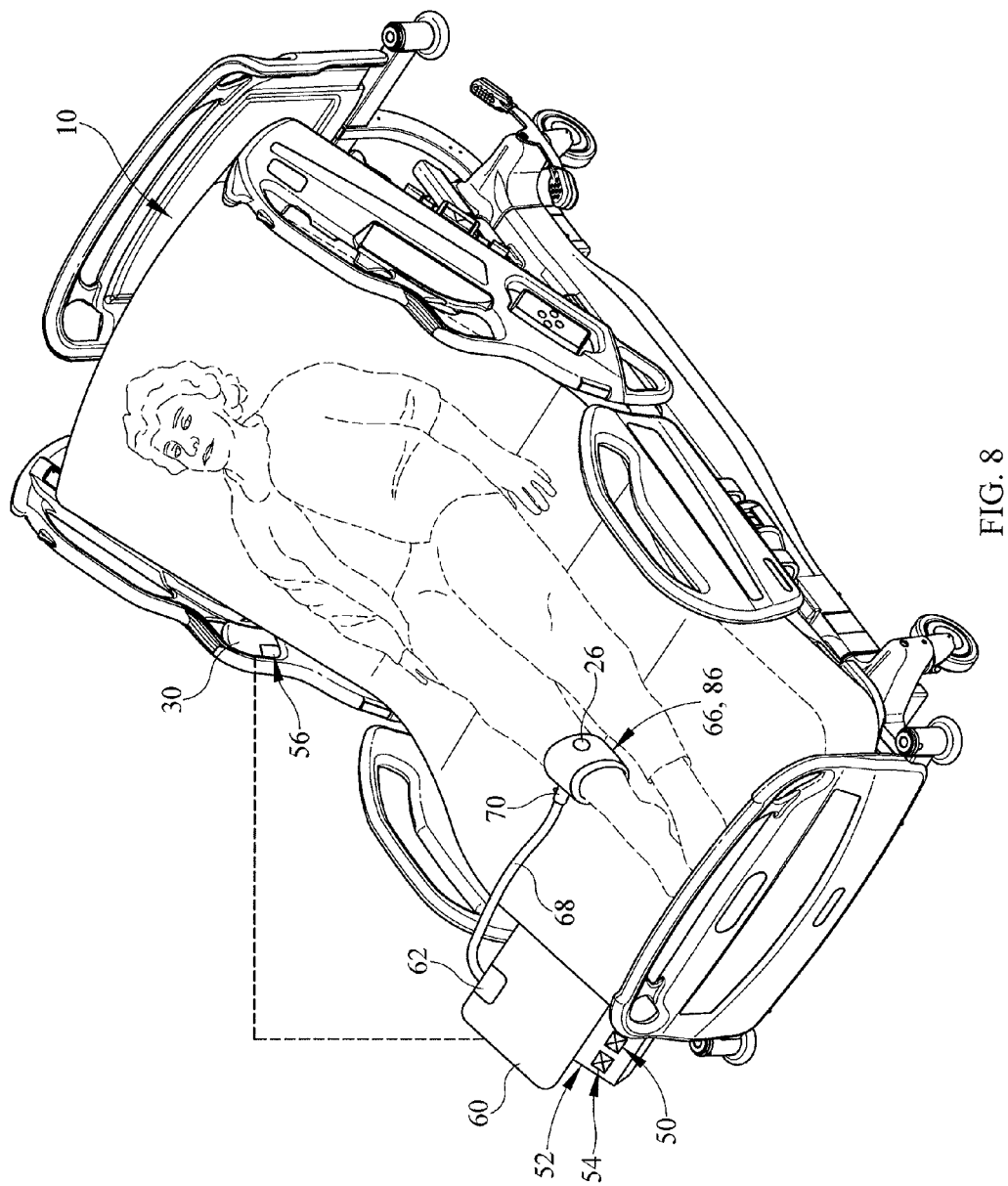
FIG. 8 is a block diagram of one system for delivery of therapeutic agents wherein the therapeutic agents are delivered via a cuff, constructed according to one or more of the principles disclosed herein.

In the embodiment shown in FIG. 8, the therapy agent repository 60 houses a controller 52. In this embodiment, the controller 52 comprises a processor 54 configured to control the operation of a therapy agent repository pump 62. The controller 52 further comprises a memory 50 in this embodiment. The controller 52 is configured to communicate with a control interface 30 to receive commands and display messages on a display device 56. In this embodiment, the control interface 30 is configured to receive a control signal to control another function of a person support apparatus 10 including but not limited to elevating a head support section, inflation and deflation of bladders of the mattress 28. Therapeutic agent is delivered to a therapy delivery cuff 66 via therapy delivery line 68 by the therapy agent repository pump 62. At least one sensor 26 is mounted on/or integrated in the therapy delivery cuff 66. The sensor 26 is configured to communicate with the controller 52 by wired connection and/or wirelessly. In the embodiment shown in FIG. 8, the therapy delivery cuff 66 is configured to be disconnected from the therapy delivery line 68 by the cuff connector 70. In this embodiment, the therapy agent repository 60 and the control interface 30 are configured to be mounted on the person support apparatus 10.

Figure 9:
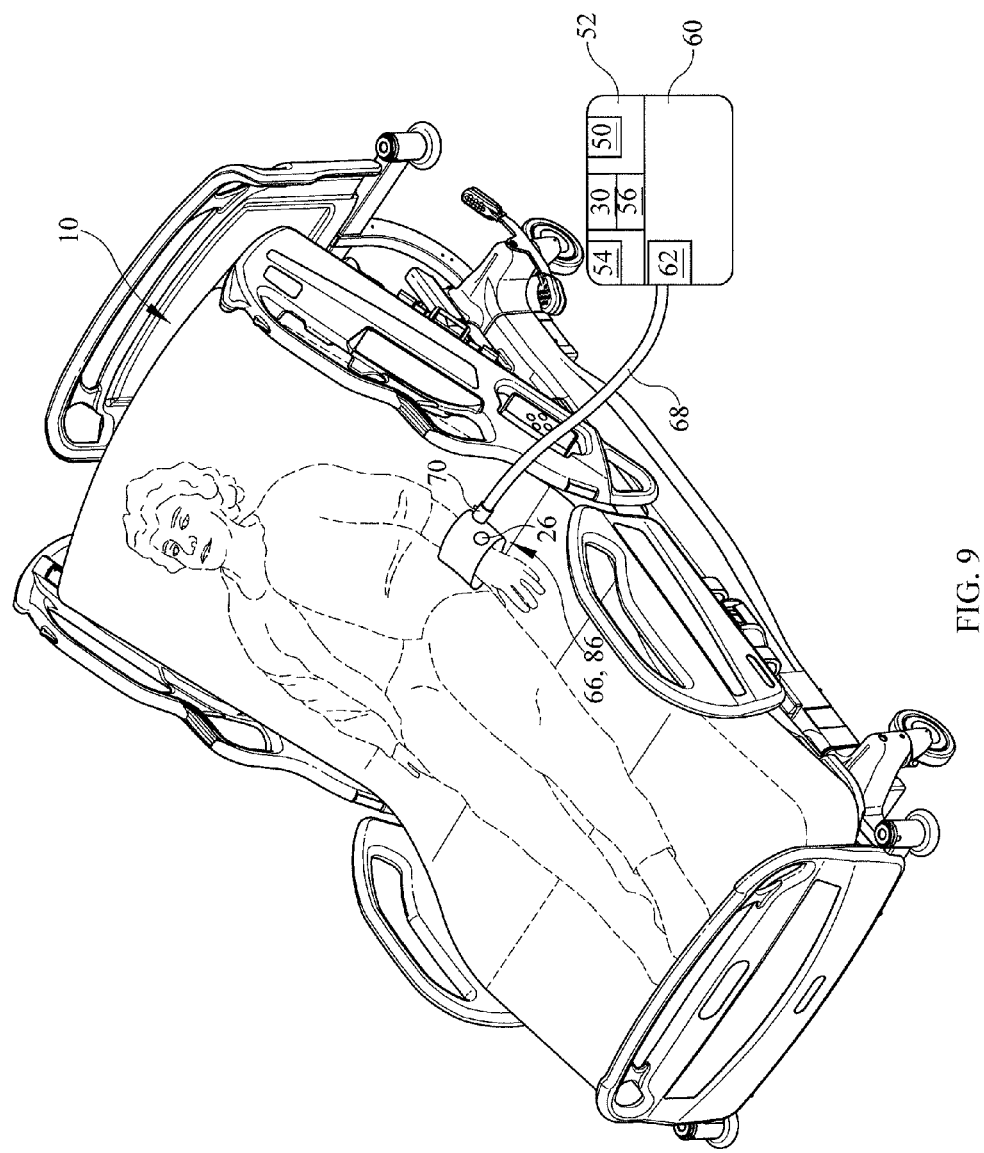
FIG. 9 is a block diagram of another system for delivery of therapeutic agents wherein the therapeutic agents are delivered via a cuff, constructed according to one or more of the principles disclosed herein.

FIG. 9 shows one embodiment of a system to deliver therapeutic agents. In this embodiment the therapy agent repository 60 is a standalone device configured to supply a therapy agent to a therapy delivery cuff 66 via a therapy delivery line 68. In this embodiment, the therapy agent repository 60 comprises a controller 52 portion and a therapy agent pump 62. The controller 52 comprises a processor 54, memory 50, control interface 30 and display device 56 in this embodiment.

Figure 10:
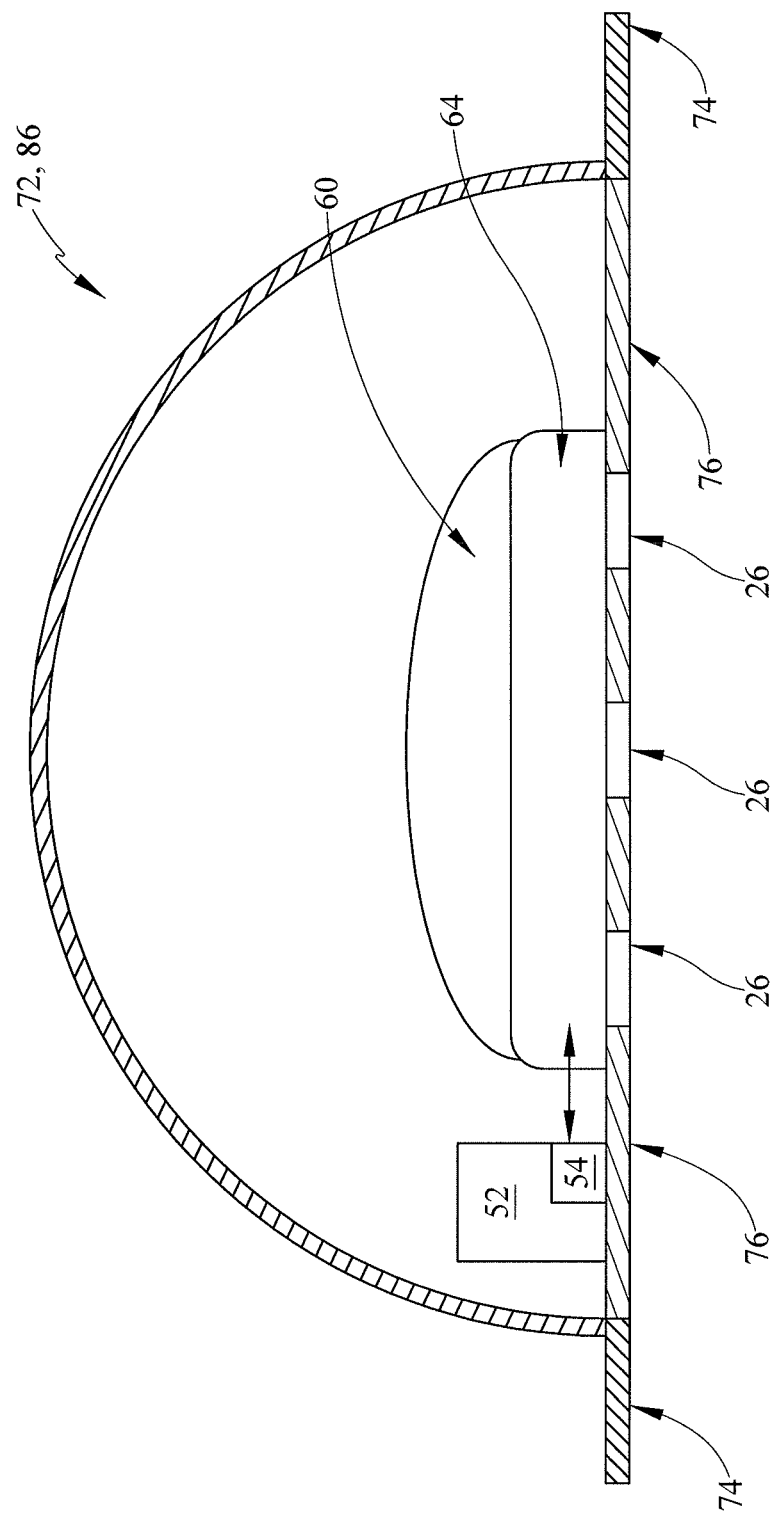
FIG. 10 is a cross-sectional representation of one system for delivery of therapeutic agents wherein the therapeutic agents are delivered via a patch, constructed according to one or more of the principles disclosed herein.

FIG. 10 is a cross-sectional representation of one embodiment of a self-contained system to deliver therapeutic agents. In the embodiment shown in FIG. 10 a therapy delivery patch 72 is configured to be attached to a portion of a patient's skin by way of adhesive patch 74. The therapy delivery patch 72 comprises sensors 26 to detect a chemical in a secretion of the patient. The sensors 26 are configured to generate a signal when a chemical is detected and communicate this signal to a controller 52. The controller 52 comprises a processor 54 which is configured to operate a therapeutic agent repository valve 64 based on analysis of the signal received from the sensors 26. The therapeutic agent repository valve 64 is configured to control flow of a therapeutic agent from a therapy agent repository 60 onto the patient's skin via a filter sheet 76 in this embodiment. In this embodiment, the filter sheet 76 also serves to separate the controller 52, valve 64 and therapy agent reservoir 60 from the patient's skin. In other embodiments, the therapeutic agent repository valve 64 may be replaced by a microfluidic pump which is controlled by the controller 52 to meter therapeutic agent onto a patient's skin.

Although FIGS. 8 and 9 show a therapy delivery cuff 66 and FIG. 10 shows a therapy delivery patch 72, both the cuff 66 and patch 72 are embodiments of a therapy delivery device 86. Any form of therapy delivery device 86 may be used in various embodiments, including but not limited to sheets, cuff, patch and clothing.

Figure 11:
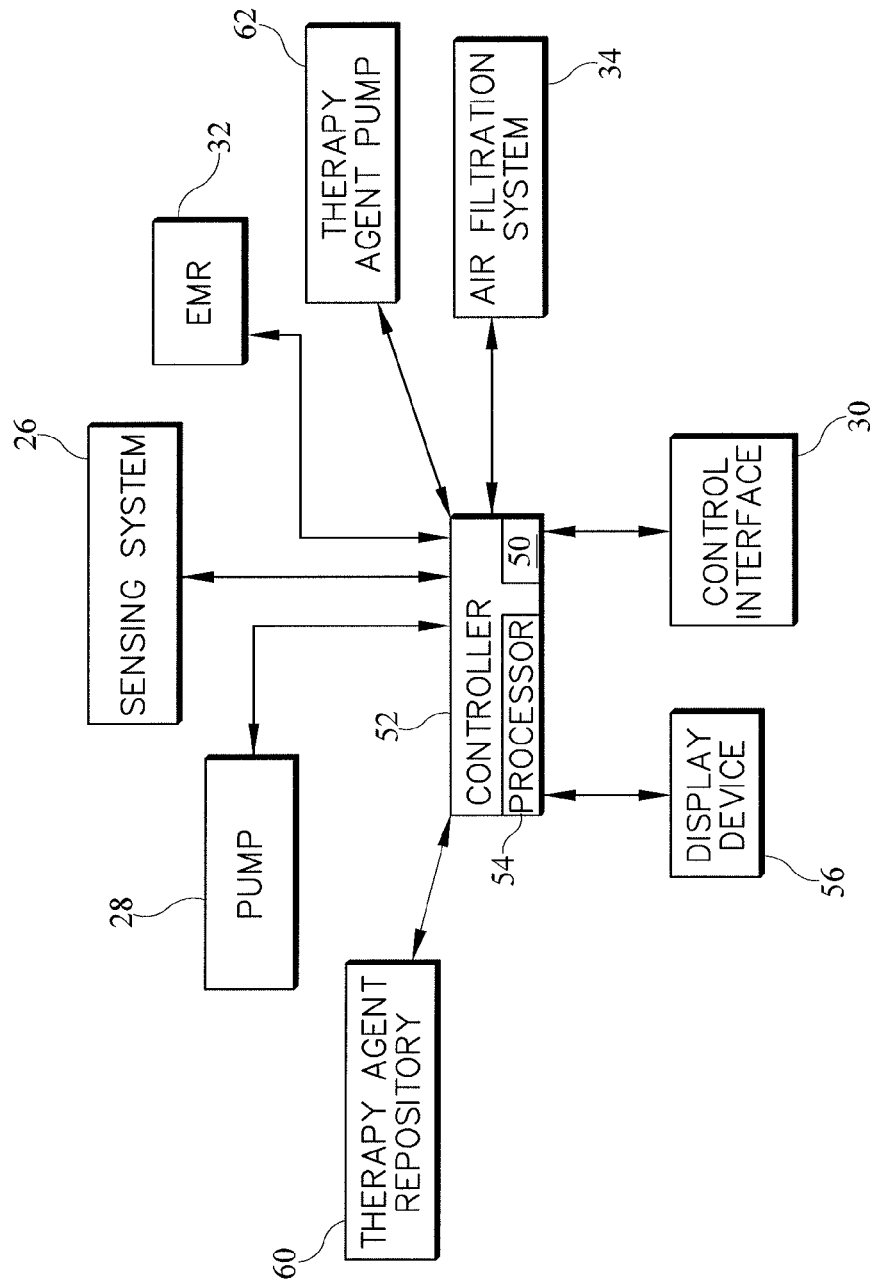
FIG. 11 is a block diagram of another system for delivery of therapeutic agents, constructed according to one or more of the principles disclosed herein.

Another contemplated embodiment of a system to deliver a therapeutic agent includes a control interface (CI) 30 in communication with a controller 52. The controller 52 is also configured to communicate with a display device 56 in this embodiment as shown in FIG. 11. In this embodiment the controller 52 comprises a processor 54 and memory 50, the controller 52 configured to communicate with a display device 56 and control interface 58. In this embodiment, the display device 56 is a monitor and the control interface 58 is a pendant. In another embodiment, display device 56 and the control interface 30 are portions of a touch sensitive screen. In this embodiment, the controller 52 is configured to communicate with the therapy agent repository 60 (to sense level of therapy agent present in the repository), therapy agent pump 62, pump 28, sensing system 26, EMR 32 and air filtration system 34.

Figure 12:
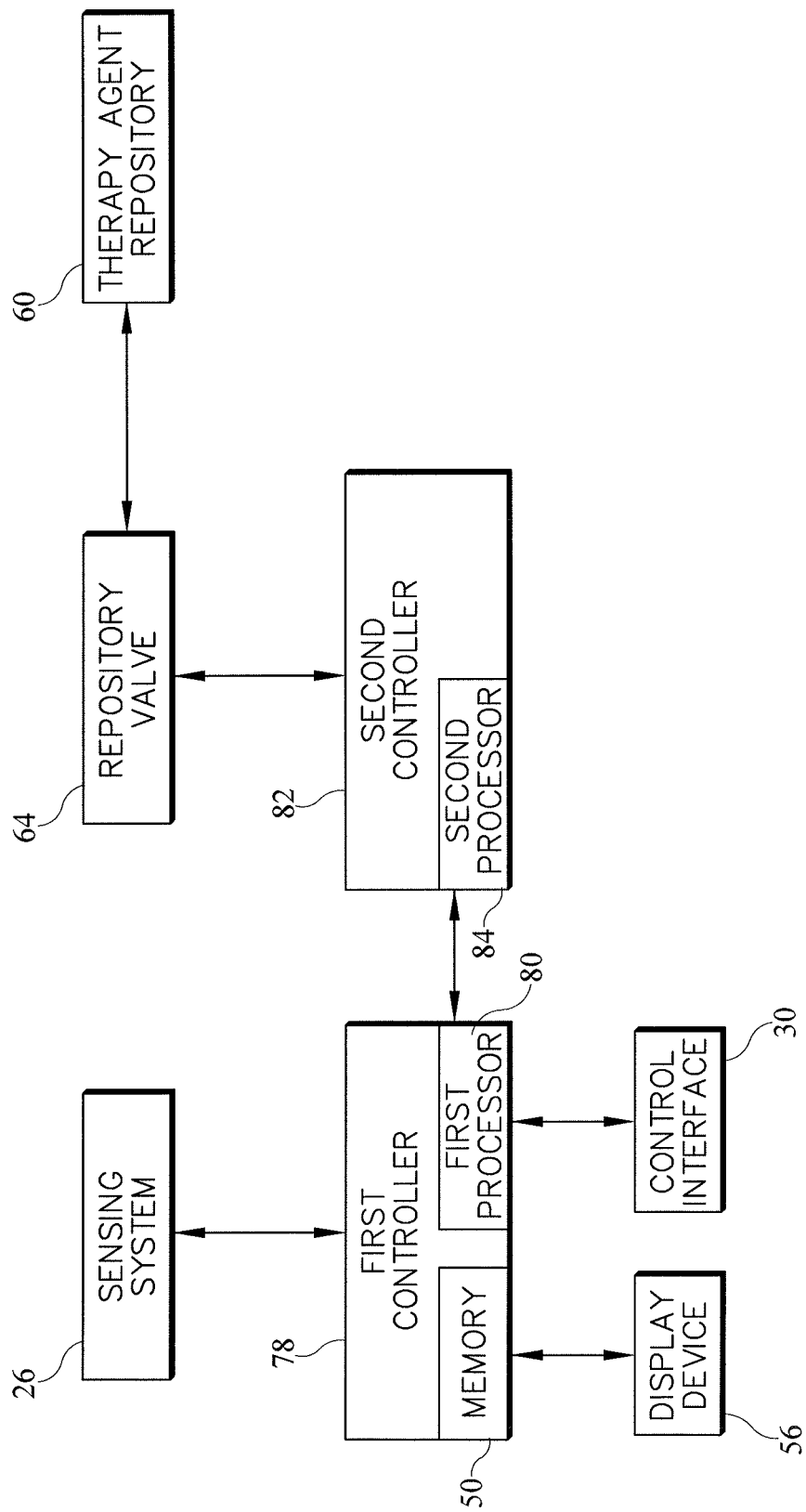
FIG. 12 is another block diagram of a system for delivery of therapeutic agents, constructed according to one or more of the principles disclosed herein.

FIG. 12 shows one embodiment of a system to deliver a therapeutic agent comprising distributed processing of information received from sensing system 26. As shown in the figure, a first controller 78 comprising a memory and a first processor 80 is configured to receive a signal from the sensing system 26. The first processor 80 in this embodiment is configured to analyze information received from the sensing system 26 to determine if the signal indicates that a predetermined threshold has been exceeded. The first processor 80 is configured to communicate the event of the predetermined threshold being exceeded to the second processor 84. The second processor 84 is configured to control a therapeutic agent repository valve 64 to release a therapeutic agent from a therapy agent repository 60. Communication between the first processor 80 and second processor 84 may be wired or wireless. The first controller 78 is configured to communicate with a display device 56 and a control interface 30 in this embodiment. In other embodiments, any of the components shown in the figure may be remote from one or more components shown and may communicate via wired or wireless systems. In other embodiments, the therapeutic agent repository valve 64 may be replaced by a microfluidic pump which is controlled by the controller 52 to meter therapeutic agent. In another embodiment, the first processor 80 is configured to share the task of analysis of the signals received from the sensing system 26 with one or more processors.

Although several embodiments have been described with components in mattresses and mattress toppers, any structure configured to support an occupant thereon, alone or in combination, may be used as a mattress and/or a mattress topper.

Although several embodiments have been described to deliver therapeutic agents, any other system to deliver therapeutic agents may be used and are within the scope of the current disclosure. In other embodiments, systems used for delivery of therapeutic agent may include but are not limited to piezoelectric pump, electro wetting system and micro-wicking system.

The use of the terms "a" and "an" and "the" and similar referents in the context of describing the subject matter (particularly in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. Furthermore, the foregoing description is for the purpose of illustration only, and not for the purpose of limitation, as the scope of protection sought is defined by the claims as set forth hereinafter together with any equivalents thereof entitled to. The use of any and all examples, or exemplary language (e.g., "such as") provided herein, is intended merely to better illustrate the subject matter and does not pose a limitation on the scope of the subject matter unless otherwise claimed. The use of the term "based on" and other like phrases indicating a condition for bringing about a result, both in the claims and in the written description, is not intended to foreclose any other conditions that bring about that result. No language in the specification should be construed as indicating any non-claimed element as essential to the practice of the invention as claimed.

Preferred embodiments are described herein, including the best mode known to the inventor for carrying out the claimed subject matter. Of course, variations of those preferred embodiments will become apparent to those of ordinary skill in the art upon reading the foregoing description. The inventor expects skilled artisans to employ such variations as appropriate, and the inventor intends for the claimed subject matter to be practiced otherwise than as specifically described herein. Accordingly, this claimed subject matter includes all modifications and equivalents of the subject matter recited in the claims appended hereto as permitted by applicable law. Moreover, any combination of the above-described elements in all possible variations thereof is encompassed unless otherwise indicated herein or otherwise clearly contradicted by context.

The disclosures of any references and publications cited above are expressly incorporated by reference in their entireties to the same extent as if each were incorporated by reference individually.

The invention claimed is:

1. A system comprising:
   a mattress on which a person lies;
   a sensor configured to generate a signal in response to a chemical that is indicative of a condition of the person;
   a therapeutic agent repository containing a therapeutic agent for treating the condition of the person; and
   a control system configured to receive said signal from said sensor and control flow of a therapeutic agent from said therapeutic agent repository to a site of the person through a portion of the mattress to treat the condition of the person with the therapeutic agent, wherein said control system comprises a first processor configured to analyze said signal and a second processor to control said therapeutic agent repository, said first processor configured to communicate with said second processor.

2. The system of claim 1, wherein said sensor is a metal oxide semi-conductor type sensor.

3. The system of claim 1, wherein said sensor is an organic semi-conducting polymer type sensor.

4. The system of claim 1, wherein said sensor is a surface acoustic wave type sensor.

5. The system of claim 1, wherein said sensor is a protein based sensor.

6. The system of claim 1, wherein said therapeutic agent repository is integrated in a mattress topper.

7. The system of claim 1, wherein said control system is configured to communicate with an electronic medical record database.

8. The system of claim 1, wherein said control system is configured to communicate with a nurse call system.

9. The system of claim 1, wherein said control system is configured to communicate with an alarm.

10. The system of claim 1, wherein said control system is configured to communicate with an air filtration system.

11. The system of claim 1, wherein said control system comprises a control interface.

12. The system of claim 1, further comprising a display configured to communicate with said control system.

13. The system of claim 12, further comprising a person support apparatus, said display configured to shown at least one indication about said person support apparatus.

14. The system of claim 1, wherein said first processor and said second processor communicate wirelessly.

15. The system of claim 1, wherein said first processor is configured to control said second processor to deliver therapeutic agent from said therapeutic agent repository to said site if said signal indicates concentration of said chemical exceeds a predetermined threshold.

16. The system of claim 1, wherein said therapeutic agent comprises at least one vasodilator.

* * * * *